(12) United States Patent
Sumaily

(10) Patent No.: US 10,299,670 B1
(45) Date of Patent: May 28, 2019

(54) SELF-RETAINING NASAL SEPTUM RETRACTOR

(71) Applicant: KING SAUD UNIVERSITY, Riyadh (SA)

(72) Inventor: Ibrahim Ali Sumaily, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/124,130

(22) Filed: Sep. 6, 2018

(51) Int. Cl.
*A61B 17/02* (2006.01)
*A61B 1/32* (2006.01)

(52) U.S. Cl.
CPC ............... *A61B 1/32* (2013.01); *A61B 17/02* (2013.01)

(58) Field of Classification Search
CPC .. A61B 17/02; A61B 17/0206; A61B 17/0218
USPC .................................................. 600/201–246
See application file for complete search history.

(56) References Cited

U.S. PATENT DOCUMENTS

| | | | | |
|---|---|---|---|---|
| 569,839 | A * | 10/1896 | Roeloffs | A61B 17/02 600/213 |
| 3,038,467 | A * | 6/1962 | Sovatkin | A61B 17/0206 600/217 |
| 3,470,872 | A * | 10/1969 | Grieshaber | A61B 17/0206 29/239 |
| 5,176,129 | A * | 1/1993 | Smith | A61B 17/0206 600/217 |
| 5,297,538 | A * | 3/1994 | Daniel | A61B 17/0206 600/206 |
| 5,529,571 | A * | 6/1996 | Daniel | A61B 17/0206 403/90 |
| 5,772,582 | A * | 6/1998 | Huttner | A61B 1/233 600/219 |
| 5,846,193 | A * | 12/1998 | Wright | A61B 17/0206 600/215 |
| 5,931,777 | A * | 8/1999 | Sava | A61B 17/02 600/210 |
| 5,993,385 | A * | 11/1999 | Johnston | A61B 17/0206 600/213 |
| 6,102,852 | A * | 8/2000 | Liu | A61B 1/32 600/219 |
| 6,196,969 | B1 * | 3/2001 | Bester | A61B 17/0206 600/219 |
| 6,224,546 | B1 | 5/2001 | Ramadan | |

(Continued)

FOREIGN PATENT DOCUMENTS

CN 201436016 U 4/2010
FR 2792821 A3 11/2000
(Continued)

OTHER PUBLICATIONS

"Horizontal Retractor," © 2013 by Precision Medical Devices, Inc., http://cenmed.com/pdf_html/or.htm, p. 84.

*Primary Examiner* — Eric S Gibson
(74) *Attorney, Agent, or Firm* — Richard C. Litman

(57) ABSTRACT

The self-retaining nasal septum retractor includes two pivotally attached arms having handles on one end and speculum blades on the opposing end. The speculum blades are adjustably connected to the arms through pivoting joints. A user can adjust the vertical displacement and angular relation between the speculum blades and the arms to fit different patient septal/nasal structures. A self-retaining mechanism allows a user to lock the retractor in a retracted position, freeing up a hand of the user for other surgical tasks.

8 Claims, 5 Drawing Sheets

(56) References Cited

U.S. PATENT DOCUMENTS

| | | | |
|---|---|---|---|
| D448,080 S | 9/2001 | Moscarelli et al. | |
| 6,302,842 B1* | 10/2001 | Auerbach | A61B 17/0206 |
| | | | 600/219 |
| 6,354,995 B1* | 3/2002 | Hoffman | A61B 1/32 |
| | | | 600/219 |
| 6,663,562 B2* | 12/2003 | Chang | A61B 17/0206 |
| | | | 600/213 |
| 6,712,825 B2* | 3/2004 | Aebi | A61B 17/025 |
| | | | 600/219 |
| 7,141,015 B2* | 11/2006 | Ruane | A61B 1/32 |
| | | | 600/220 |
| D566,268 S * | 4/2008 | Koros | D24/135 |
| 7,481,766 B2* | 1/2009 | Lee | A61B 17/02 |
| | | | 600/214 |
| D617,456 S * | 6/2010 | Ott | D24/135 |
| 9,301,674 B2* | 4/2016 | Fritzinger | A61B 1/32 |
| 9,408,596 B2* | 8/2016 | Blain | A61B 17/0218 |
| 9,550,277 B1* | 1/2017 | Williams | A61B 17/8866 |
| 2002/0133060 A1* | 9/2002 | Doyle | A61B 1/233 |
| | | | 600/210 |
| 2004/0024291 A1* | 2/2004 | Zinkel | A61B 17/0206 |
| | | | 600/218 |
| 2005/0027170 A1* | 2/2005 | Nohara | A61B 17/0206 |
| | | | 600/219 |
| 2005/0215864 A1* | 9/2005 | Jang | A61B 17/0206 |
| | | | 600/217 |
| 2005/0267336 A1* | 12/2005 | Bertolero | A61B 1/313 |
| | | | 600/219 |
| 2007/0213596 A1* | 9/2007 | Hamada | A61B 17/02 |
| | | | 600/219 |
| 2009/0187081 A1 | 7/2009 | Kelly | |
| 2012/0064484 A1* | 3/2012 | Hassani | A61C 3/00 |
| | | | 433/144 |

FOREIGN PATENT DOCUMENTS

| | | |
|---|---|---|
| JP | 2010119455 A * | 6/2010 |
| WO | 9908587 A1 | 2/1999 |

\* cited by examiner

SELF-RETAINING NASAL SEPTUM RETRACTOR

BACKGROUND

1. Field

The disclosure of the present patent application relates to surgical retractors, and particularly to a self-retaining nasal septum retractor having adjustable speculum angles.

2. Description of the Related Art

Surgical instruments have been designed in order to provide minimally invasive visual and physical access to the inner nose and certain areas within the human head, such as the suprasellar and parasellar areas. With the introduction of rhinoscopy in the mid-nineteenth century, a variety of nasal specula were designed for nasal and transnasal surgery. Nasal specula have evolved to incorporate many different shapes and sizes tailored for specific procedures and patient abnormalities. Currently, endoscopic sinus surgery is one of the most common surgeries for either sinus pathology or as an approach to intracranial pathology, which has triggered new advances in retractor and speculum features.

During the performance of nasal surgery, several separate instruments are required to be inserted through a very narrow nasal opening. Specula have been designed to spread and protect the nostril tissue, including the septum, but the ridged relation between the handle and the specula can prevent a user from positioning the specula in a desired location. This is especially the case when a large portion of the device remains in the working area just below the nose. Unobstructed movement is necessary in this area in order to operate other surgical instruments inserted in the nostril. Constant readjustment or accidental movement of the speculum can cause unnecessary damage to the patient, potentially affecting the outcome of the procedure.

In cases where the patient has a deviated septum, a typical nasal speculum will not create a proper opening for the surgeon to operate. In such cases, surgeons commonly perform a septoplasty to improve the view and ease of instrument insertion to the surgical field. This additional procedure is time consuming and carries additional risk to the patient. In cases where the deviated septum is not symptomatic to the patient, which is often the case, the septoplasty will not afford the patient an improvement. Therefore, there is a need for a retractor capable of retracting a deviated septum.

Thus, a nasal septum retractor solving the aforementioned problems is desired.

SUMMARY

The self-retaining nasal septum retractor includes two pivotally attached arms having handles on one end and speculum blades on the opposing end. The speculum blades are adjustably connected to the arms through pivoting joints. A user can adjust the vertical displacement and angular relation between the speculum blades and the arms to fit different patient septal/nasal structures. A self-retaining mechanism allows a user to lock the retractor in a retracted position, freeing up a hand of the user for other surgical tasks.

A method of nasal retraction includes inspecting a patient's nostril to document unique and irregular structures. Once a topographical understanding of the patient's nasal septum has been achieved, a user can adjust the speculum pivots to conform to the structures of the patient's septum. An adjusted retractor is then inserted into the nostril and the speculum blades are positioned on the previously determined features. Retraction using the adjusted speculum blades will create a large working corridor within the nostril for the user to perform the procedure. Once the procedure is finished the retractor is removed from the nostril and either sterilized or thrown away.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
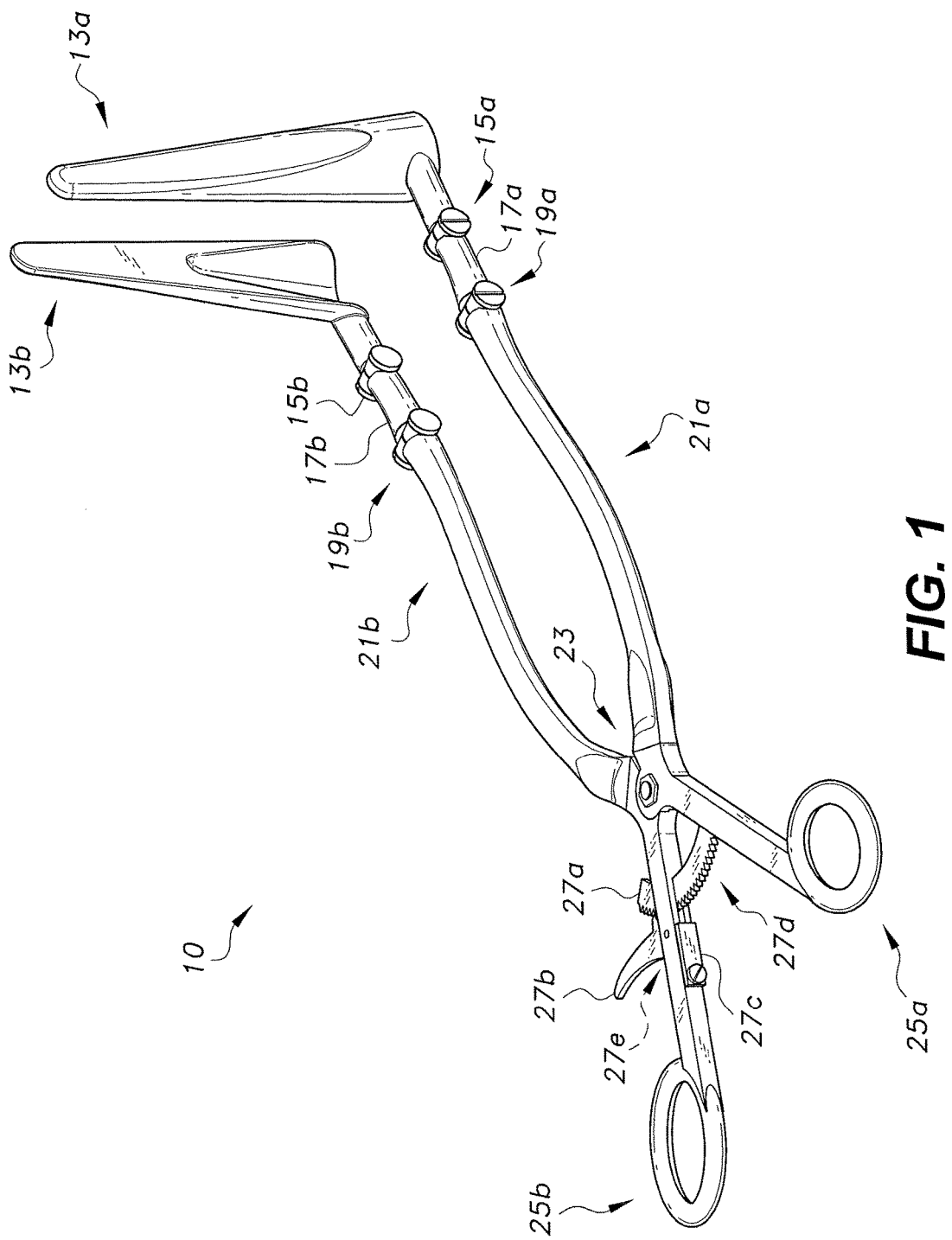
FIG. 1 is a perspective view of a self-retaining nasal septum retractor.

The self-retaining nasal septum retractor provides a self-retaining vertically and angularly adjustable nasal septum retractor 10. Referring to FIG. 1, the retractor 10 includes a pair of arms 21a, 21b, which are pivotally connected. Handles 25a, 25b having finger loops are located at the proximal end of the arms for a user to engage with the fingers and thumb to operate the instrument. The distal ends of the arms are attached in series to joints 19a, 19b, 15a, 15b, which pivotally attach speculum blades 13a, 13b to the arms. A self-retaining mechanism 27a, 27b, 27c, 27d, 27e is capable of locking the arms 21a, 21b at a desired opening (spacing) and angular relation to one another.

The first arm 21a and second arm 21b are connected by a joint 23 including a pivot pin that extends through a bore in each of the arms 21a, 21b, providing the arms with a pivotal relationship. The arms 21a, 21b are connected as a non-cross joint, which is chosen because joining the proximal handle portions will cause the speculum blades to spread. This configuration may be preferred because a user will have more control and power when contracting with the hand than when extending. Alternatively, the arms 21a, 21b may be configured as a cross-hinge for procedures where less force is necessary. The arms 21a 21b are bowed outwardly to give the user an expanded working field when the retractor 10 is in a retracted state. The preferred embodiment shows the portion of the arms distal to the arm joint 23 longer that the proximal portion with the handles 25a, 25b. This configuration allows for a magnitude increase between the input movement at the handle and the output movement at the speculum. Alternatively, the distal portion can be shorter than the proximal portion resulting in a force increase at the output end, but also a magnitude decrease.

The proximal end of the retractor 10 is shown with the handles 25a, 25b comprising rings or loops for accepting a user's fingers. Alternatively, other user grips/interfaces known in the art may be used for their respective benefits. Further, an electrically driven mechanism may be used to control the pivotal relationship between the arms 21a, 21b. An electrical drive may allow for more precision with regard to distance and force.

The distal ends of the first arm 21a and second arm 21b are each connected to respective intermediate members 17a, 17b by respective speculum joints 19a, 19b. A bore in the proximal end of each intermediate member 17a, 17b is aligned with a bore in the distal end of their respective arms 21a, 21b. A hinge pin in inserted through the aligned bores of the first arm 21a and intermediate member 17a, and another hinge pin is inserted through the aligned bores of 21b and 17b to create the joints. Each intermediate member is connected at its distal end to a respective speculum blade 13a, 13b by distal speculum joints 15a, 15b having a hinge mechanism similar to the proximal speculum joints 19a, 19b. The hinges have variable stiffness, allowing the user to tighten the joint to a desired stiffness. Preferably, a stiffness light enough to be flexed by the user's hands, in preparation for the procedure, while remaining stiff enough to maintain the preset position during the procedure. It is also contemplated that the joints have a locking feature for giving the user the ability to easily adjust the joint to a desired position and then be locked in place. For example, the self-retaining nasal septum retractor 10 may have a configuration having teeth on the connected members' bore adjacent surfaces, which are in contact with the each other, and a threaded hinge pin that can be tightened to compress the surfaces together. While only a hinge pin joint is discussed, any joint orientation known in the art is contemplated for these joints. In a preferred embodiment, the speculum joints 15a, 15b, 19a, 19b are restricted to operate in a plane perpendicular to the plane of the arm connecting joint 23. These joints 15a, 15b, 19a, 19b allow a user to adjust the angle of the intermediate members 17a, 17b and the speculum blades 13a, 13b with respect to the arms 21a, 21b. The intermediate members 17a, 17b give the proximal end of the speculum blades 13a, 13b the ability to be displaced from the plane on which its arm 21a, 21b lies. Thus, the speculum blades 13a, 13b can move with three degrees of freedom. Devices with only one or greater than two speculum joints are also contemplated. Further, it is also contemplated to incorporate speculum blade joints that also allow lateral adjustment for situations where a lateral angle or displacement is desired.

Figure 2:
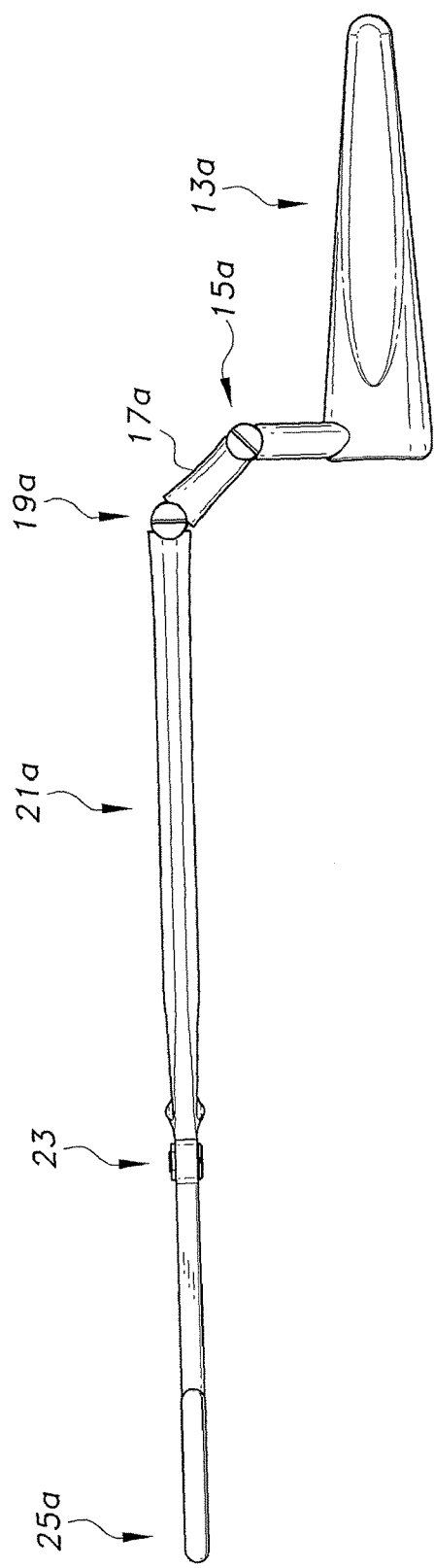
FIG. 2 is a side elevation view of the self-retaining nasal septum retractor of FIG. 1.

FIG. 2 shows a side view of the device with both sets of speculum joints in the same position. Therefore, only the first arm 21a components are depicted. This view shows a possible vertical and angular orientation of the medial intermediate member 17a and speculum blade 13a. In this orientation, the proximal speculum joint 19a is angled downward, which displaces the distal speculum joint 15a (and therefore the respective speculum blade 13a) vertically below the plane of the arm 21a. The distal speculum joint 15a is also angled down to reorient the tip of the speculum blade 13a so it is in a plane parallel with the arm 21a.

The individual adjustability of the speculum blade joints 15a, 15b, 19a, 19b allows a user to adjust each speculum blade 13a, 13b for contacting an optimal location in the patient's nose with regard to potential retraction size and protection of the intranasal tissue. In cases where the patient has a deviated septum, standard retractors typically will not create a large enough working area due to the irregular septal surface, thus preventing proper retraction. By adding adjustability to both angular deviation and vertical displacement with respect to the device arms 21a, 21b, a user can adjust the blade 13a to a position where it can properly contact the irregular surface of the septum. This may prevent the need for a septoplasty in many cases when it would not be necessary for other reasons. The angular deviation and vertical displacement of the speculum blades 13a, 13b will be determined and set on a case-by-case basis based on the unique structure of each nostril.

Figure 3:
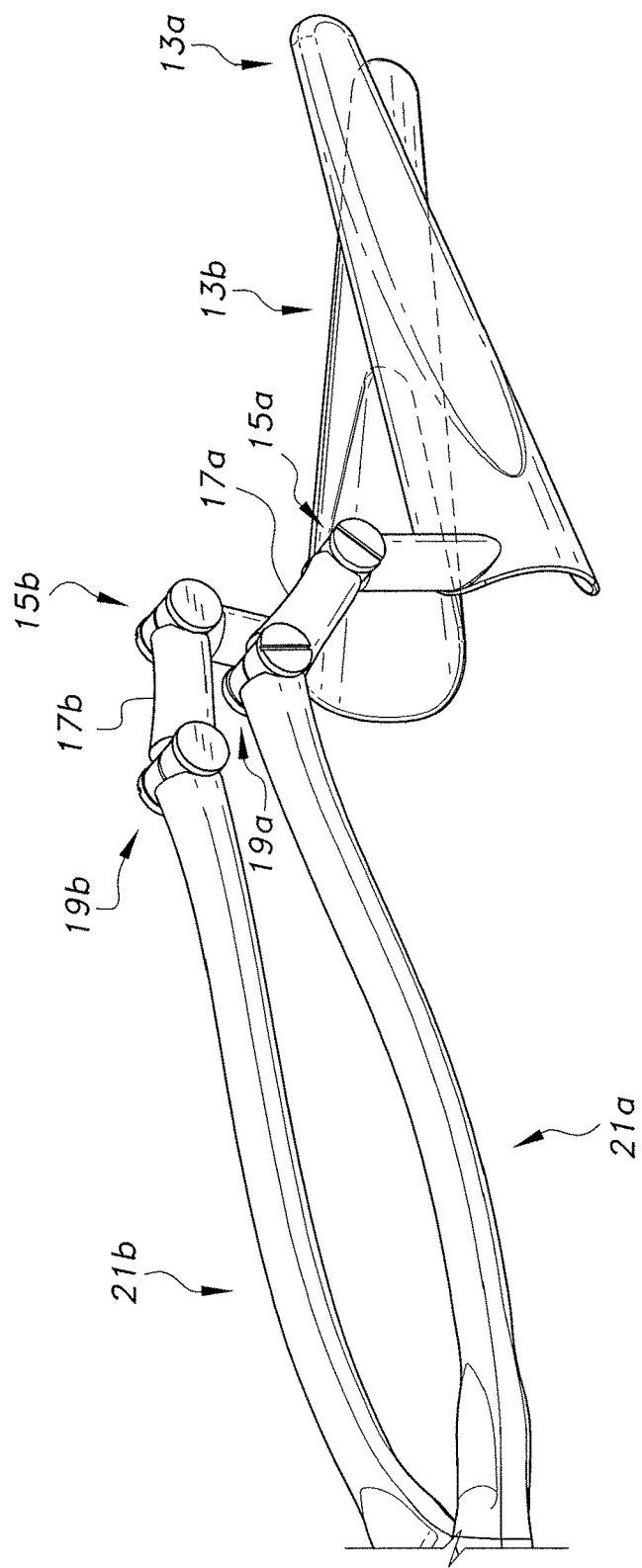
FIG. 3 is a partial side elevation view of the self-retaining nasal septum retractor of FIG. 1, showing the nasal speculum blades set to a desired orientation before surgery.

FIG. 3 depicts the retractor 10 in a preset position that may be set by a user after inspection of the patient's nasal features and before insertion into the nostril. As seen in FIG. 3, the configuration takes advantage of the individual angular adjustability of each speculum blade 13a, 13b. The proximal speculum joint 19b of the lateral speculum blade 13b is at a slight downward angle of deviation, since minimal vertical offset is necessary, and the distal speculum joint 15b of the corresponding blade 13b is set to a downward angle. The speculum blade 13b can be used to retract and protect the patient's inferior turbinate. In this hypothetical patient, the location of the inferior turbinate is slightly more posterior that a typical patient, so that the speculum blade 13b has been adjusted to contact the turbinate's center. The speculum blade 13a, adjusted for contacting the septum, is positioned for a situation where the hypothetical patient's deviated septum is more accepting of a blade coming from a lower vertical position and at an upward angle. Therefore, the speculum joint 19a of the first arm 21a is angled more sharply downward than the proximal speculum joint 19b of the lateral speculum blade 13b, utilizing the intermediate member 17a for vertical displacement, and the distal speculum joint 15a is angled only slightly downward to create the necessary upward angle of the speculum blade 13a from the lower position. This is purely a hypothetical configuration, as each patient will require different adjustment based on the procedure and nostril characteristics. The angles in FIG. 3 are exaggerated to help depict the features being discussed.

Figure 4:
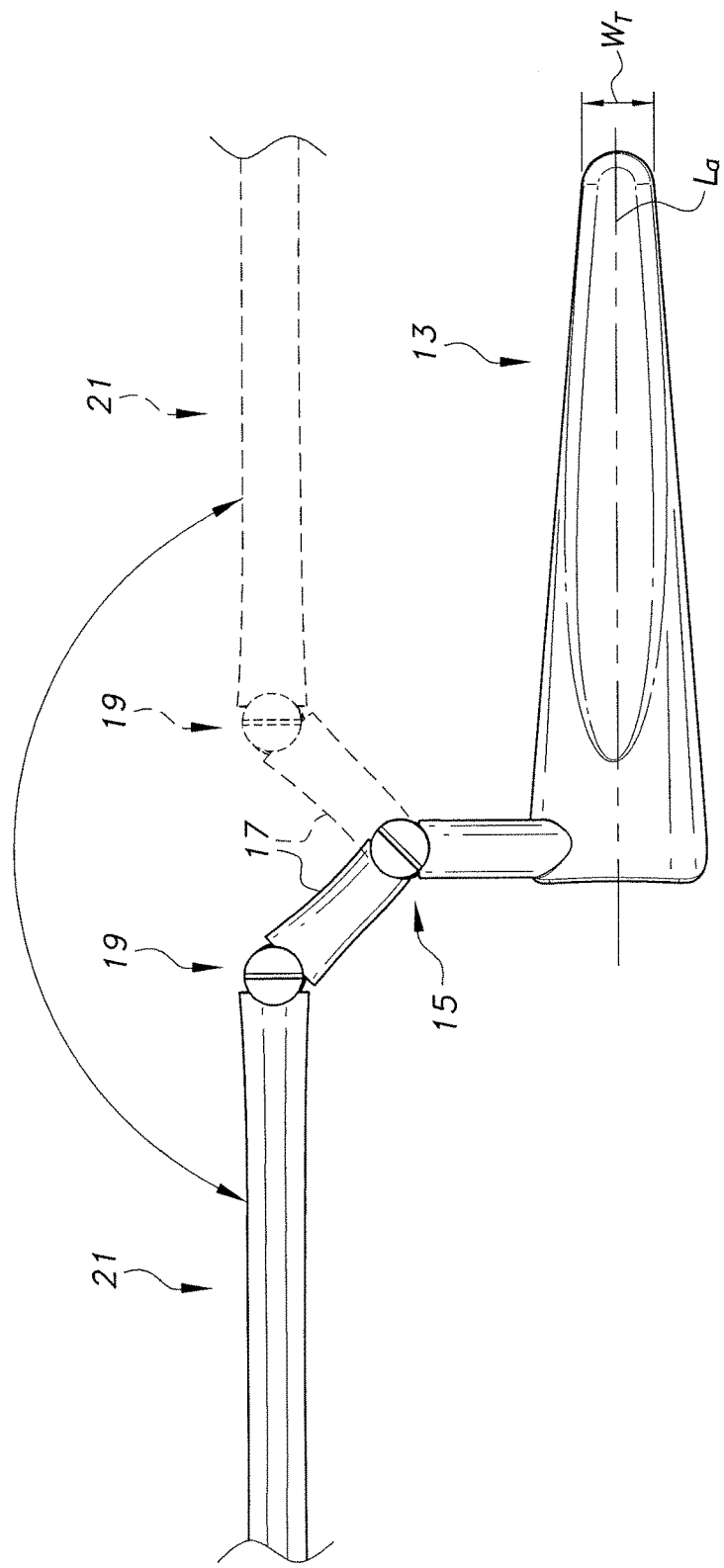
FIG. 4 is a partial side elevation view of the self-retaining nasal septum retractor of FIG. 1, shown both in an insertion configuration and in a working configuration.

FIG. 4 shows a change in the angle of the proximal speculum joints 19 and distal speculum joints 15 that can be performed during a procedure. In the first configuration, shown in solid lines, both joint angles are downward, similar to the orientation in FIG. 2. This orientation may be advantageous for insertion of the speculum blades 13 into the nostril because it allows a user to align the speculum blades 13 with the arms 21, while slightly displacing the arms 21 so that there is a direct line of sight between the blades 13 and into the nose. Once the septum and nostril are retracted, a surgeon will typically insert multiple tools, often including a rigid endoscope and forceps, which are operated by lengthy handles. A relatively large movement of the handle may be necessary for a small movement of the tool head. Accordingly, a large working area below the nose may be required. If the retractor 10 maintains its position in the location directly below the nostril, it may hinder the movement of the user, potentially increasing the time of the operation or decreasing the quality of work performed. Therefore, it would be beneficial to move the non-critical portions of the retractor 10 out of this working area. The dashed lines show the retractor 10 in a second orientation that would be advantageous for the portion of the operation where instruments are inserted into the nostril. The speculum joints 15, 19 are pivoted up so the handles 25 and arms 21 are positioned above the patient's head, giving the user an unobstructed working area to maneuver the handles of the tools inserted in the nostril.

Referring back to the preferred embodiment illustrated in FIG. 1, the blades 13a, 13b of the speculum are designed in a way that avoids damaging the tissue within the nostril when inserted, retracted, and adjusted. This is achieved through preventing points of high stress, which may damage the tissue. The end of the blades 13a, 13b and all of their edges are rounded to remove sharp points that can cut the tissue or provide points of stress concentration. A superior edge of each blade 13a, 13b tapers out from the distal to proximal end in order to match the shape of the nostril. By shaping the blades 13a, 13b according to the shape of the nostril channel, the blades 13a, 13b maintain contact with a maximum surface area on the sides of the nostril without adding undue stress due to conflicting shapes. Each blade 13a, 13b curves inward around its longitudinal axis, providing an external surface that matches the shape of the nostril entrance.

The retractor 10 should create a large working corridor for visualization inside the nostril and to give the user an area to work within the nostril. The curved shape of the speculum blades 13a, 13b creates a conical working corridor for the tools to access the inner nose or trans-nasal region. The tools cannot be designed with the same non-damaging characteristics as the speculum blades 13a, 13b, since they need to perform their intended functions, which, in many cases, include damaging tissue. For instance, a knife must to be sharp in order to properly perform its duties of cutting. The corridor created by the speculum blades 13a, 13b provides a necessary protective barrier for the surrounding tissue. When a knife is inserted into the nostril, contact will be made with the speculum blades 13a, 13b, instead of the tissue, thereby preventing possible damage to the tissue.

The speculum blades 13a, 13b may specifically be designed for different procedures where various size and shape characteristics are beneficial. For example, a trans-nasal procedure, including procedures in the sellar, infrasellar, and supraseller regions, may benefit from having longer blades with a less severe taper at the tip. This will allow the blades to be inserted further into the nostril, creating a longer protective corridor. Trans-nasal blades may also flair out slightly at the distal-most end. The outward flair can further retract soft tissue directly adjacent the site of the tissue being operated on, giving the user more space to visualize the area and maneuver the multiple tools.

Alternatively, the speculum blades 13a, 13b may be specifically designed for intra-septal procedures. Often, a patient's septum may be an irregular shape, which won't properly conform to the shape of a generic speculum blade. In these cases, it may be beneficial to contour the outer edge or surface of the septum-contacting speculum blade to match or counter the septum's shape. In other instances where specific mucoperichondral flaps or turbinates need to be retracted, the blade intended to engage these specific structures can be shaped in a way that optimizes retraction.

Figure 5:
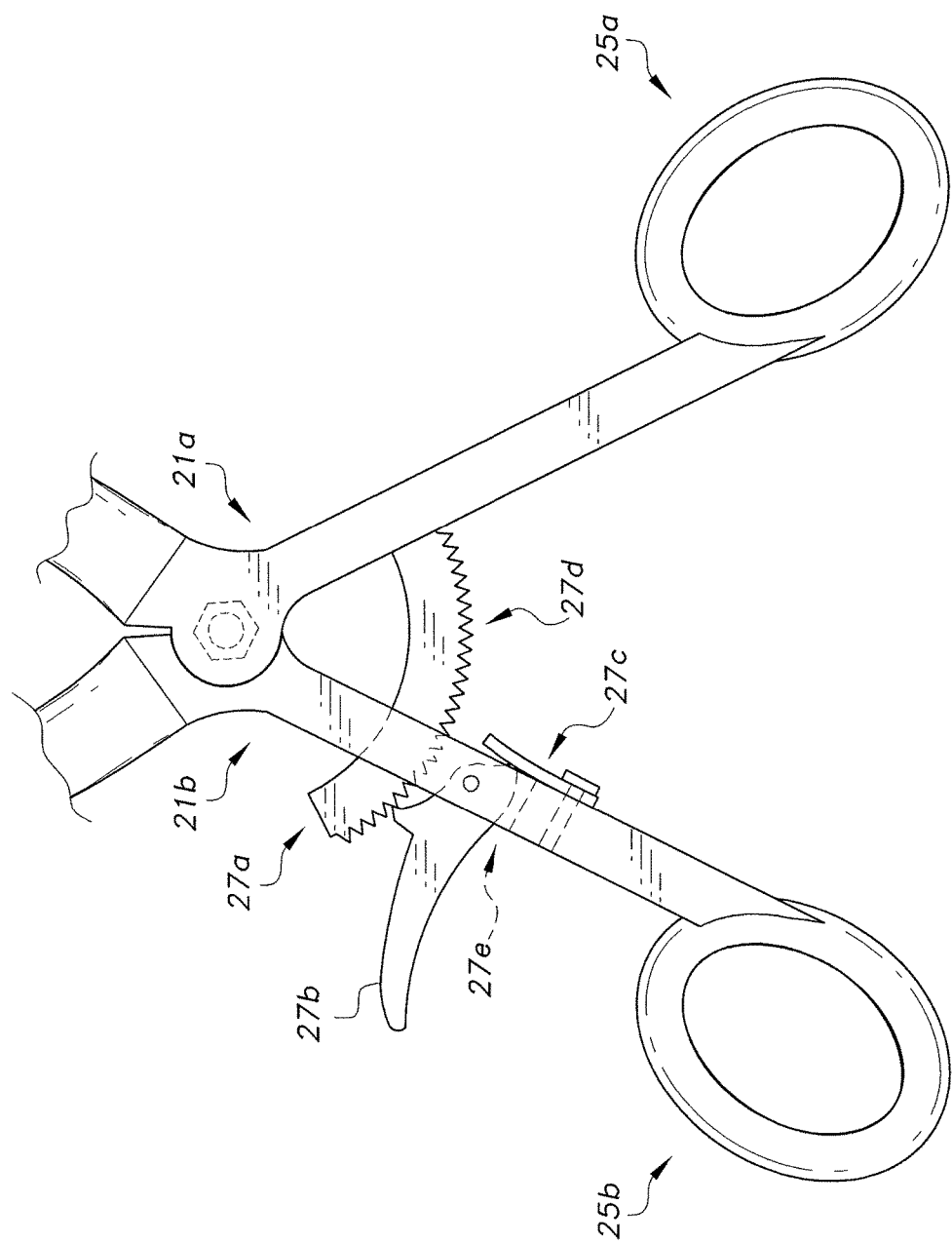
FIG. 5 is a partial top view of the handle and locking mechanism of the self-retaining nasal septum retractor of FIG. 1.

FIG. 5 shows an embodiment of the self-retaining mechanism 27a-27e. The self-retaining mechanism 27a-27e allows a user to lock the arms 21a, 21b at a specific angular relation to one another, therefore maintaining a retracted state without requiring a user to hold the instrument. This affords the user a free hand for use in other aspects of the procedure.

The self-retaining mechanism 27a-27e in FIG. 5 comprises an arcuate guide 27a attached at its one end to the first arm 21a with the lateral end extending through a hole 27e in the second arm 21b. When pivoting the arms 21a, 21b, the guide 27a slides freely through the hole 27e, guiding the relative movement of the arms 21a, 21b. A lower surface of the guide 27a is fitted with a row of extending teeth 27d spread across its length. The teeth 27d are configured to engage a locking handle 27b attached to the freely pivoting arm 21b, thereby preventing the arm 21b from sliding freely on the guide 27a, effectively locking it in place. The locking handle 27b is connected to the lateral arm 21b by a locking holder 27c which biases the locking handle 27b towards the teeth 27d in order to maintain the locked position, in which teeth on the locking handle 27b are mated with the teeth 27d on the guide. A user can unlock the self-retaining mechanism 27a-27e to change the angular relation between the arms 21a, 21b by applying a proximally directed force to the locking handle 17b with a free finger. The force exerted by the user will overcome the bias set by the locking holder 27c and separate the locking handle 27b from the teeth 27d. Once the teeth 27d and locking handle 27b are separated, the arms 21a, 21b can freely pivot to any desired angular relation. The device may also include a mechanism for locking the handle in a freely movable position so that the user doesn't not need to maintain pressure on the handle in situations where locking is not necessary or a hindrance. Alternatively, other locking mechanisms known in the art are contemplated for use with this device. Such mechanism may include a threaded bolt that adjusts the width through twisting the bolt or an electrically powered locking mechanism that the user operates through a user interface.

The retractor 10 described above may be manufactured out of stainless steel, titanium, cobalt-chromium alloys or any other biocompatible metals having proper strength and stiffness characteristics. The external metal surface present the risk of reflecting light into the user's eyes during an inspection, especially when a user is shining a beam of light into the nostril. Therefore, it may be beneficial to ebonize the surfaces of the instrument as a measure to prevent light reflection.

Disposable retractors 10 may be made out of polymers, such as polypropylene, polyvinyl chloride, polycarbonate, polyurethane, polyethersulfone, polytetrafluoroethylene, polyetherimide, polysulfone, or any other biocompatible polymers having proper strength and stiffness characteristics.

The speculum blades 13a, 13b are contemplated as being within the range of 2 cm to 8 cm in length, preferably 5 cm, along their longitudinal axis $L_a$, which is the axis directed into the nostril when inserted. The tip width $W_T$ of the speculum blades 13a, 13b, the portion spanning the nostril passage, is contemplated to be within the range of 4 mm to 12 mm, preferably 8 mm. The intermediate members 17a, 17b connecting the two speculum joints 15, 19 are contemplated as being within the range of 0.5 cm to 3 cm in length, preferably 1 cm. This distance from the arm joint 23 connecting the handles 25 to the proximal speculum joints 19 is contemplated as being within the range of 5 cm to 15 cm, preferably 10 cm. Nasal structures are sized and shaped differently on different people. Therefore, sizes outside of these ranges are contemplated when a patient's features require the instrument to have a dimension not listed.

The speculum joints 15, 19 are contemplated as having up to three hundred and sixty degrees of rotation, and the arm joint 23 is contemplated as having up to 180° of rotation. However, it is understood that different joint configurations can restrict the angular range.

A method of nasal retraction with the above described retractor may begin with an inspection, by a surgeon, of the nostril that is being retracted. The surgeon takes note of specific feature, such as the location of the inferior turbinate and/or shape and location of a septum deviation. Based on the findings, the surgeon will adjust the proximal speculum hinges 19 and distal speculum hinges 15, separately for each of the speculum blades 13a and 13b to a location the surgeon believes will offer the best retraction and protection for the patient. The speculum blade 13*a* is adjusted based on the shape of a user's septum and the speculum blade 13*b* is adjusted based on the opposing wall feature being retracted, typically the inferior turbinate. The user may test the adjusted retractor 10 in the patient's nostril and readjust if necessary. The properly oriented speculum blades 13 are then inserted into the patient's nostril with the blade 13*a* placed against the septum and the blade 13*b* placed against the opposing wall, typically against at least the inferior turbinate. Once the retractor 10 is inserted and checked for proper position, the user will spread the speculum blades 13 by pulling on the locking handle 27*b* to separate the teeth 27*d* and then squeeze the handles 25 to retract the speculum blades. A minimal amount force is exerted by the user to prevent damage to the patient's nostril tissue. If the device fails to satisfactorily retract the nostril, a user may adjust the position or angles of the speculum blades. Once the nostril is satisfactorily retracted, the locking handle 27*b* is released by the user, locking the retractor in its retracted position. At this point, the arms 21 and handles 25 of the retractor 10 may be pivoted up above the patient's forehead to create more space below the nose for performing the procedure. The surgeon proceeds with the procedure by using the working channel created by the speculum blades 13, making sure to use the curved speculum blades 13*a*, 13*b* as guides for the tools so that damage to surrounding tissue is minimized. Once the procedure is completed, the user will pull on the locking handle 27*b*, separating it from the teeth 27*d* of the locking guide 27*a*, and close the speculum blades 13*a*, 13*b* for removal.

Some procedures this device may be used for include submucosal resection of the nasal septum (S.M.R.); septo-rhinoplasty; removal of suprasellar, sellar, and infrasellar tumors; microscopic sinus or otic surgery; myringtomy and grommet insertion; polypectomy; and stapedectomy. This is by no means an exhaustive list but it gives an indication of many procedures than can use the described retractor. The retractor 10 may also be used for other surgical procedures requiring retraction in locations other than the nose.

It is to be understood that the self-retaining nasal septum retractor is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A self-retaining nasal septum retractor, comprising:
   a first arm and a second arm, each of the arms having a proximal portion, a distal portion, and an intermediate portion between the proximal portion and the distal portion;
   an arm joint pivotally connecting the first and second arms at their intermediate portions;
   a first intermediate member and a second intermediate member;
   a first nasal speculum blade and a second nasal speculum blade, each of the speculum blades consisting of an elongated blade portion and an integral connecting portion disposed perpendicular to the elongated blade portion;
   a first proximal speculum joint pivotally connecting the first intermediate member to the distal portion of the first arm and a second proximal speculum joint pivotally connecting the second intermediate member to the distal portion of the second arm, the first and second proximal speculum joints being independently adjustable, wherein the independent adjustability is a user-adjustable pivoting stiffness;
   a first distal speculum joint pivotally connecting the first nasal speculum blade connecting portion directly to the first intermediate member and a second distal speculum joint pivotally connecting the second nasal speculum blade connecting portion directly to the second intermediate member, the first and second distal speculum joints being independently adjustable, wherein the independent adjustability is a user-adjustable pivoting stiffness; and
   a self-retaining mechanism attached to the first arm and the second arm, the self-retaining mechanism selectively locking the first and second arms with the first and second nasal speculum blades at a user-selectable angular separation.

2. The self-retaining nasal septum retractor according to claim 1, wherein:
   the self-retaining mechanism comprises an arcuate guide rigidly attached to the first arm;
   the second arm has a guide aperture defined therein, the guide being slidable through the guide aperture in the second arm.

3. The self-retaining nasal septum retractor according to claim 2, wherein:
   the arcuate guide has a lower surface and a plurality of teeth extending from the lower surface; and
   the self-retaining mechanism further comprises a locking handle pivotally attached to the second arm, the locking handle having at least one interlocking tooth extending therefrom selectively interlocking with the teeth extending from the lower surface of the arcuate guide to prevent further pivoting of the first and second arms relative to each other, the locking handle being pivotal between a locked position in which the at least one tooth is interlocked with the teeth extending from the lower surface of the arcuate guide and an unlocked position in which the arcuate guide is free to slide through the guide aperture.

4. The self-retaining nasal septum retractor according to claim 1, wherein the proximal and distal speculum joints pivot in a plane perpendicular to a plane in which the arm joint pivots.

5. The self-retaining nasal septum retractor according to claim 1, wherein each speculum elongated blade portion has a longitudinal axis, each speculum elongate blade portion being curved around its own longitudinal axis in a direction toward the opposing speculum blade.

6. The self-retaining nasal septum retractor according to claim 1, wherein each of the speculum blades have a peripheral edge, wherein each of the peripheral edges are configured to be smooth and rounded to prevent tissue damage.

7. The self-retaining nasal septum retractor according to claim 1, wherein the proximal portions of said first arm and said second arm each define finger loops adapted for grasping by a user with fingers and thumb to pivot said arms to separate said nasal speculum blades to a selectable angle for retraction of a nasal septum.

8. The self-retaining nasal septum retractor according to claim 1, wherein the proximal and distal speculum joints permit independent adjustment of said first and second nasal speculum blades relative to said first and second arms for retracting a patient's nasal septum to allow sufficient room for access for endoscopic surgical instruments.

\* \* \* \* \*